United States Patent
Soane et al.

(10) Patent No.: US 6,821,509 B2
(45) Date of Patent: Nov. 23, 2004

(54) NANOSCOPIC HAIR CARE PRODUCTS

(75) Inventors: David S. Soane, Piedmont, CA (US); Matthew R. Linford, Orem, UT (US)

(73) Assignee: Cosmetica, Inc., Emeryville, CA (US)

(*) Notice: Subject to any disclaimer, the term of this patent is extended or adjusted under 35 U.S.C. 154(b) by 0 days.

(21) Appl. No.: 10/269,272

(22) Filed: Oct. 11, 2002

(65) Prior Publication Data

US 2003/0072728 A1 Apr. 17, 2003

Related U.S. Application Data

(63) Continuation of application No. PCT/US01/11970, filed on Apr. 13, 2001.
(60) Provisional application No. 60/197,766, filed on Apr. 14, 2000.

(51) Int. Cl.$^7$ .................................................. A61K 7/06
(52) U.S. Cl. .................................... 424/70.11; 424/70.1
(58) Field of Search .............................. 424/70.1, 70.2, 424/70.6, 70.11, 70.13

(56) References Cited

U.S. PATENT DOCUMENTS

| | | | |
|---|---|---|---|
| 3,653,952 A | 4/1972 | Gagliardi | 117/126 GN |
| 4,665,107 A | 5/1987 | Micale | 523/105 |
| 5,286,629 A | 2/1994 | Denis et al. | 435/7.1 |
| 5,372,804 A | 12/1994 | Khoshdel et al. | 424/59 |
| 5,641,561 A | 6/1997 | Hansen et al. | 442/417 |
| 5,756,080 A | 5/1998 | Janchitraponvej et al. | 424/70.122 |
| 5,919,487 A | 7/1999 | Simonnet et al. | 424/490 |
| 6,277,404 B1 | 8/2001 | Laversanne et al. | 424/450 |
| 6,379,683 B1 * | 4/2002 | Simonnet et al. | 424/401 |
| 6,413,527 B1 | 7/2002 | Simonnet et al. | 424/401 |
| 6,500,446 B1 | 12/2002 | Derrieu et al. | 424/408 |

FOREIGN PATENT DOCUMENTS

| | | |
|---|---|---|
| EP | 0 573 229 | 12/1993 |
| WO | WO 90/11069 | 10/1990 |
| WO | WO 98/46199 | 10/1998 |
| WO | WO 01/06054 | 1/2001 |
| WO | WO 01/43859 | 6/2001 |
| WO | WO 01/62376 | 8/2001 |

* cited by examiner

Primary Examiner—Jyothsna Venkat
(74) Attorney, Agent, or Firm—Jacqueline S. Larson

(57) ABSTRACT

The present invention is directed to a hair treatment preparation comprising a payload in an intimate relationship to a polymeric nanostructure, the polymeric nanostructure being reactive to hair or capable of being immobilized onto or in hair. The nanoscopic nature of the entities being engineered ensures three distinct characteristics. First, the imparted attribute can be either nearly permanent or semi-permanent, depending on the attachment chemistry. In the semi-permanent version, the intended effect can be controllably erased by removal of the nanostructure by simple chemical or physical means. Second, the nanoscopic entities are invisibly small. Their presence does not deteriorate the hand or feel of the hair. Third, the nano-technology approach is infinitely flexible and adaptable. It can be coupled with many existing dyes, colorants, UV absorbers, fragrances, softening agents and the like for hair treatment. Methods for treating hair with the hair treatment preparations of the invention are also encompassed.

19 Claims, 1 Drawing Sheet

NANOSCOPIC HAIR CARE PRODUCTS

The present invention is a continuation of co-pending International Patent Appln. No. PCT/US01/11970, filed Apr. 13, 2001 and designating the United States of America, which application claims the benefit of Provisional U.S. application Ser. No. 60/197,766, filed Apr. 14, 2000; the entire disclosures of both of which are incorporated herein by reference.

FIELD OF THE INVENTION

The present invention is directed to the field of hair care products.

BACKGROUND OF THE INVENTION

Human hair, like animal wool, horn, nails, skin, and feathers, etc., comprises proteinaceous helices known as keratins. Such structural proteins degrade with prolonged exposure to sunlight, harsh chemicals such as dyes and bleach, and air-borne pollutants. Hair follicles also stop producing the requisite melanin as a person ages; thus, the hair turns gray. To preserve a youthful appearance or for fashion purposes, the cosmetic industry has developed conditioners and coloring agents for hair. In addition, fragrances and UV blockers have been incorporated into shampoos and conditioners to further impart desirable attributes. However, the technical approaches traditionally adopted to achieve these objectives have been developed in an ad hoc fashion.

Current hair dyes and dying systems involve harsh chemicals, such as oxidizing agents, to convert pigment precursors into colored species after such precursors are first applied to the hair. This basic approach requires the precursors to penetrate deeply into the hair shaft, whereupon the oxidative conversion takes place in a subsequent operation. Similarly, when lighter colors or shades are desired, the bleaching agents must diffuse deeply into the hair to destroy the intrinsic melanin deposits. Repeated dying or bleaching using harsh chemicals tends to damage the hair significantly. Scalp exposure to the chemicals also may induce allergic reactions in sensitive individuals.

SUMMARY OF THE INVENTION

This invention provides a systematic nanoscopic platform to enable a comprehensive list of hair care products. In one embodiment, this invention provides a technology platform for developing hair-coloring products that do not require oxidizing or bleaching chemicals. The nano-technology platform is based on an entirely different premise for coloring. In a similar manner, conditioning effects, UV-blocking abilities, and prolonged fragrance release can be achieved with this invention. The nano-technology platform offers advantages that have not been achievable by other means to date.

More particularly, this invention is directed to a hair treatment preparation comprising a dye or other payload with an intimate relationship to a polymeric nanostructure, the nanostructure having hair-reactive functional groups or other characteristics that allow it to be covalently bound to or otherwise immobilized onto or in the hair. This invention describes a systematic approach where nanoscopic objects or structures are either shaped as a miniature sphere or particle that can be attached to a hair, referred to herein as a "nanosphere" or a "nanoparticle"; or as an invisibly small, molecular-dimensioned net surrounding a hair, referred to herein as a "nanoscopic macromolecular network" or "nanoscopic polymer network".

The nanospheres and nanoscopic networks are constructed out of polymeric materials, which can be either naturally occurring or synthetic. The natural kind can be modified or derivatized by well-established organic chemistry. The synthetic type can be specially designed to exhibit custom-tailored properties.

The above geometries are merely examples of the whole spectrum of nano-technology that is applicable to the hair product industry. Many variations of the two basic schemes can be envisioned and are intended to be covered by this invention. For example, mixtures of nets and spheres can be developed to give more than one attribute per treatment. In addition, the nets can be fully crosslinked (either chemically or physically) or partially crosslinked. They can even be an entangled but not crosslinked network. The net may further be attached to the hair or to another polymeric species deposited on the hair surface at sparsely distributed points, so that the molecular network resembles a collection of nanoscopic whiskers. The spheres may be formed as micelles, where a group of surfactant molecules capture a payload, the resulting micelle being crosslinked after or upon deposition onto hair through a mordant or a polyelectrolyte.

Regardless of the geometrical features, the nanoscopic nature of the entities being engineered ensures three distinct characteristics. First, the imparted attribute can be either nearly permanent or semi-permanent, depending on the attachment chemistry. In the semi-permanent version, the intended effect can be controllably erased by removal of the nano-structure by simple chemical or physical means. Second, the nanoscopic entities are invisibly small. Their presence does not deteriorate the hand or feel of the hair. The impact of the nanoscopic objects or structures can at most be felt as enhanced smoothness or softness. Third, the nano-technology approach is infinitely flexible and adaptable. It can be coupled with many existing dyes, colorants, UV absorbers, fragrances, and softening agents for hair treatment.

The present invention is further directed to methods of treating hair which comprise applying a hair treatment preparation to the hair, the hair treatment preparation comprising a payload in an intimate relationship to a polymeric nanostructure, the polymeric nanostructure being reactive to hair or capable of being immobilized onto or in the hair; and changing the conditions such that the payload and nanostructure are attached to the hair.

DETAILED DESCRIPTION OF THE INVENTION

Figure 1:
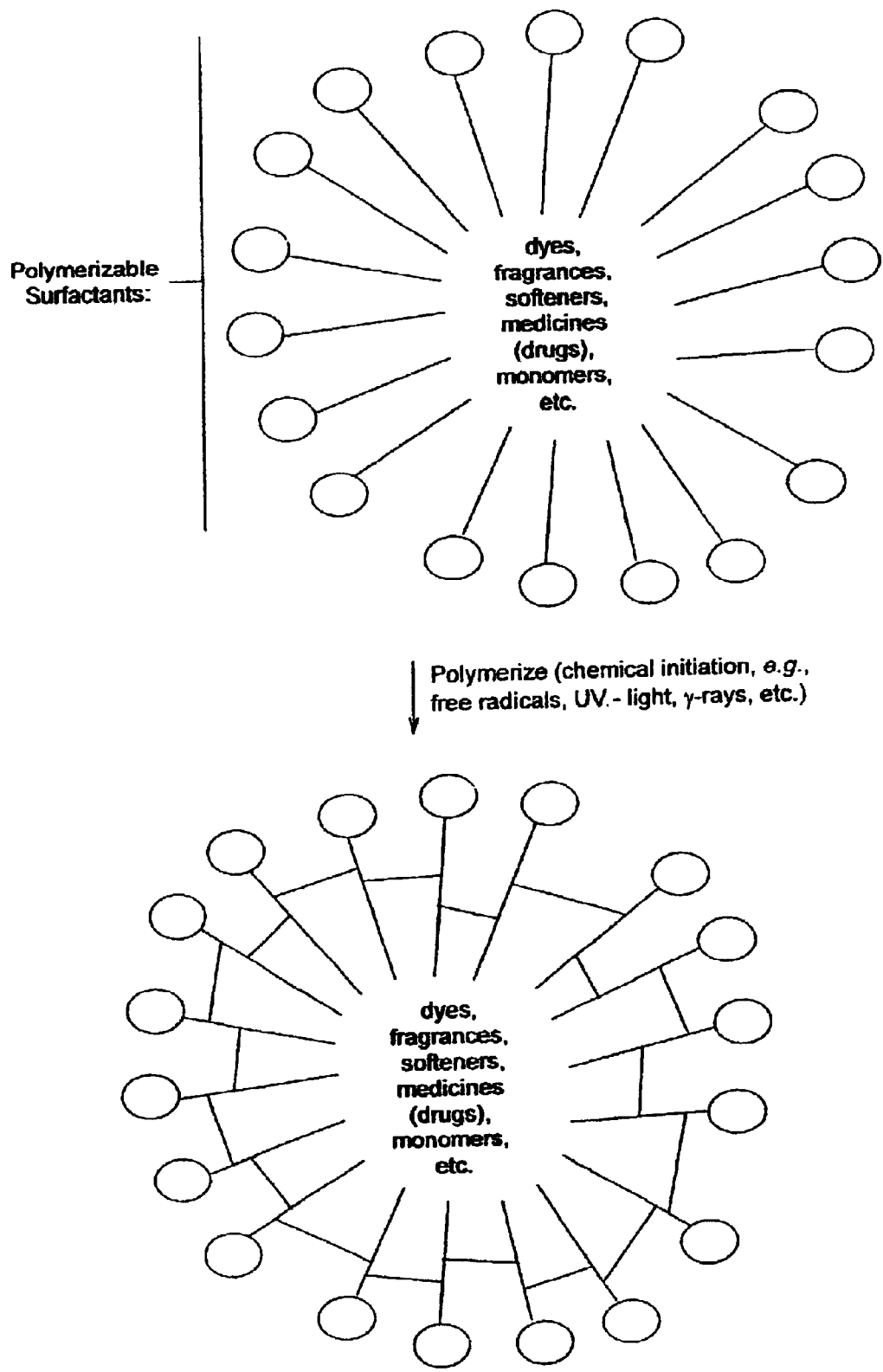
FIG. 1 is a schematic representation of one embodiment of a nanoparticle of the present invention, and the method of preparing it by the sequestration of a payload of dyes, fragrances, softeners, medicines (drugs), monomers and the like, into a micelle by polymerizable surfactants, which are then polymerized to make the nanoparticle with a specified interior.

The hair treatment preparations of the invention comprise an agent or payload in permanent or semi-permanent intimate relationship with a polymeric nanostructure, the polymeric nanostructure being reactive to (such as by covalent bonding) or capable of being immobilized onto or in hair. In one embodiment, the polymeric nanostructure may include hair-reactive functional groups for binding or attachment of the nanostructure to the hair to be treated.

By "intimate relationship" is meant that the payload is surrounded by, contained within, chemically attached to or otherwise in permanent or semi-permanent relationship with the polymeric nanostructure.

By "hair-reactive" is meant that the payload-containing nanostructure will form a covalent bond with the hair.

The terms "payload" and "payload agent" as used herein refer collectively to any material or agent that would be desirable for permanent or semi-permanent attachment to or treatment of human or animal hair. It may modify a property of hair or may add new and desirable properties to the hair. The payloads are also referred to herein as "pendant groups". The payload may be, but is not limited to, dyes or coloring agents, pigments, opacifying agents, scents and fragrances, drugs and pharmaceuticals, softeners, insect repellents, antibacterials and antimicrobials, and the like. While the following discussions herein are directed to certain exemplary agents, it is important to note that other materials having any desirable activity or characteristic suitable for hair treatments may also be incorporated into polymeric nanostructures according to the teachings herein and are included within the scope of this invention.

By "dye" is meant a molecule that can absorb wavelengths in the visible or ultraviolet region of the electromagnetic spectrum.

Nano-technology is an emerging field of study, where the objects/structures are nanoscopic in dimension. The word "nano" means one-billionth. Therefore, objects characterized by dimensions of 1 nanometer to 1 micron (1 micrometer, or 1000 nanometers) fall within the range of nano-technology.

Nano-Technology Based Coloring Systems

The power of nano-technology is evidenced by its ability to allow the designed products to segregate or partition engineering requirements into different parts of the system. Instead of requiring the coloring agents or their precursors to penetrate deeply into the hair shaft, the nanoscopic entities may simply be deposited on the surface of the hair strand or only partially penetrate into the interior. Durability or semi-permanency may be the result of, for example, how the nanoscopic structure attaches itself to the hair or crosslinks amongst neighboring entities or crosslinks through a fixative. In the latter two versions, the nanoscopic entities do not have to form direct linkages with the hair itself. In all versions, the nanoparticles or nanoscopic networks are only carriers for the active ingredients (e.g., hair dye). They themselves do not have to be colored intrinsically. Their primary functions are two-fold. First, they must provide a means to anchor themselves on the surface or shallow interior of hair. Second, they must encase or encapsulate the correct dosage of dyestuff (in the case of nanospheres or nanoparticles) or have the dyestuff linked to the carrier (in the case of nanoscopic networks). Note that nanoparticles may assume other, non-spherical shapes, yet may be equally capable of performing the same functions.

In either direct attachment or indirect anchoring, the nano-technology approach does not resort to high temperature or extreme pH or harsh chemicals, the use of which will compromise the goal of this invention. Examples of attachment/anchoring are presented below. Those who are skilled in the art of polymer precipitation and complexation will undoubtedly envision additional means of securing the nanospheres based on the teachings herein. These are all intended to be covered by the spirit and scope of this disclosure.

The above concepts are illustrated by the examples below. First, with respect to nanospheres or nanoparticles, the payload, for example dye molecules or their aggregates (referred to collectively herein as "dyestuff"), is entrapped, that is, surrounded by or contained within a polymer shell or matrix. The nanoparticle of the invention may comprise a polymeric shell surrounding the payload or it may comprise a three-dimensional polymeric network entrapping the payload, both of which are referred to herein as a "polymer shell". Alternatively, in the case of hair dyes, if a lighter color/shade is desired, some or most of the particles will contain blocking agents, such as colloidal white pigments (e.g., titanium oxide or zinc oxide). Mixed with these whitening or opacifying agents are nanoparticles containing dyestuff. The overall system yields the desired color/shade, once the mixed particles are deposited on the hair.

The nanospheres may be made of non-toxic, non-allergenic polymers. Many polymers have been approved by the FDA for topical usage. Silicones and cellulosics, among many others, are salient examples. Synthetic hydrocarbon-based polymeric systems are equally suitable alternatives. Proteins or synthetic peptides can also be used for this purpose. Well-established encapsulation techniques exist to encase the right amount of dye in particles of controlled size distribution. Literature abounds in both processing and material information to achieve this objective.

However, in the present invention, the surface of the nanoparticles contain functional groups for binding or attachment to the hair, to provide permanent or semi-permanent attachment of the payload to the hair. Alternatively, the surface of the nanoparticle includes functional groups that can bind to a linker molecule that will in turn bind or attach the particle to the hair. In either case, these functional groups are referred to herein as "hair-reactive functional groups".

The chemical linkage on the surface of the nanoparticle does not involve the molecules of the payload. The payload agents are physically entrapped within the nanoparticle, thus requiring no chemical modifications of the payload molecules themselves. The resulting encapsulated payload preparations or nanoparticles have improved retention within and on the hair structure without changing the inherent character of the payload agent.

The payload-containing nanoparticles may be formed via one of several methods of encapsulation known in the art, such as interfacial polymerization, microemulsion polymerization, precipitation polymerization, and diffusion. Multi-component mixture preparation followed by atomization/spraying into a drying chamber is yet another processing scheme. Reactive functional groups on the polymer shell provide a means for attaching the hair treatment nanoparticles to human hair.

The nanoparticles of the invention are formed by contacting a payload with a set of monomers, oligomers, or polymers (referred to herein as a "polymeric set"). The monomers, oligomers, or polymers assemble around the payload and then are polymerized, with or without crosslinking, into a polymeric network or shell surrounding the payload. The polymeric set in one embodiment includes at least some components that provide reactive functional groups on the surface of the final polymeric bead, which will bind to the hairs to be treated.

Alternatively, a nanoparticle optionally having hair-reactive functional groups on its surface can first be prepared by polymerizing a polymeric set, after which a payload can be exposed to the bead under suitable conditions such that the payload is absorbed into and entrapped in the polymeric network or shell, to provide the hair-reactive payload nanoparticle.

Particular monomers, oligomers, or polymers useful in forming the nanoparticles of the present invention are those that contain amine, hydroxyl, or sulfhydryl monomers or polymers combined with amine-, hydroxyl-, or sulfhydryl-reactive monomers or polymers.

Along the backbone of the polymer constituting the nanospheres, hair-reactive functional groups may be introduced that may either be chemically reactive under mild conditions or be electrostatically interactive with complementary groups on the surface of the hair when the ionic strength or surfactant content of the medium is shifted by rinsing. Example interactions include charge-charge, dipolar, hydrogen-bonding, hydrophobic, or dehydration interactions. The nanospheres may be made of a polyelectrolyte with an isoelectric point in the range of alkaline pH. These particles may be effectively precipitated or aggregated by using another polyelectrolyte (linear or branched polymer fixative) that possesses an acidic isoelectric point. When the hair is first exposed to the nanospheres and then is re-exposed to the second polyelectrolyte fixative, a complex forms in situ, coating the treated hair.

Another route is the use of a potent surfactant formulation to carry the payload-containing nanoparticles to the hair surface in a finely divided dispersion. Once in place, the surfactant is rinsed away, leaving the nanoparticles adhering strongly to the treated hair. An example is silicone-based nanoparticles. Such particles can be easily dispersed in a block or graft copolymer of poly(dimethylsiloxane-ethylene glycol) liquid. The latter medium may be rinsed away by water, as the component is water-soluble, leaving the insoluble nanoparticle as an adherent precipitate. Functionalized siloxanes can further refine this precipitation principle by utilizing complexation as well. For example, siloxanes with carboxylate side groups may be precipitated by the dual use of removing the surfactant and adding a polyamine (such as polyethyleneimine in the aqueous rinse solution). Conversely, amino-substituted siloxanes can form an in situ crosslinked network with the nanoparticles embedded within by the addition of polyacids (such as polyacrylic acid or polymaleic acid or copolymers thereof.

Complexation can also be induced by addition of polyvalent cations or anions, each reactive towards the complementary charged surface groups.

The principle of thermodynamics-induced and complexation-induced precipitation/anchoring on hair surfaces can be equally applied to other synthetic or naturally occurring nanostructures. For example, the payload can first be chemically coupled onto a protein carrier. This protein-payload complex is dispersed in a medium, which is then applied to the hair. A change in the thermodynamic balance of the medium causes deposition of the complex on the surface of hair. The hair is thus treated. Since coupling is carried out chemically outside the presence of hair, traditional chemical means can be used without fear of hair degradation or skin sensitivity. Protein deposition can then be effected by simpler, milder fixative reactions.

We reiterate the power of delegating different engineering requirements to different parts of the system. The color comes from the dyestuff contained within the nanoparticles. Yet, the controlled degree of permanency stems from the attachment methodology. The above precipitation/complexation approach can be made difficult to reverse or it can be easily reversible. Reversibility can be engineered to occur only in the presence of certain specific agents. Therefore, normal hair wash or shampoo does not cause fading of the color. For example, functionalized silicones are difficult to wash away, unless specific siloxane-containing surfactants such as block or graft copolymers of siloxane-polyethylene glycol are used. Equivalently, complex or precipitate dissolution may or may not occur under similarly engineered rinsing conditions. Thus, the artificially-created hair color can be either preserved in a prolonged manner or reversed when desired.

Note that derivatized cellulosics can be made to function in a similar way. Synthetic polypeptides can also be used for dyestuff encapsulation. Such cellulosic or proteinaceous surfaces can be modified to exhibit varying isoelectric points, which can be exploited to tailor their precipitation/coagulation/complexation properties.

Nanospheres are but one geometry as a possible dye or other payload carrier. Dye molecules can also be attached to linear, branched, or lightly crosslinked polymer carriers, as long as they remain soluble or dispersible in a suitable (aqueous or mixed aqueous) and chemically mild liquid. Dye fixation onto hair is implemented through reaction/precipitation/complexation on the surface of hair via any of the above-illustrated and many other schemes. Imagine the dye-attached polymer having a tree-like architecture. As long as residual functional groups exist after the dye is attached onto the tree, the whole ensemble may be deposited on the surface of hair in a subsequent operation (removal of surfactant, addition of precipitant, introduction of coagulating or complexing agent, etc.). Even if no discernible functional groups remain after the initial dye attachment, the carrier still may have great utility simply due to its ability to adhere firmly to hair as a consequence of a shift in the thermodynamic environment of the medium.

One group of polymers useful as nanostructures in the present invention are the dendrimers and other highly branched polymers. Dendrimers also have a high degree of symmetry. Because such polymers are branched, they are compact and so good penetration, and thus permanency, into hair is expected. Dendrimers and highly branched polymers can be designed to have one or more different types of functional groups on them. Using these functional groups, dye molecules, alkyl or siloxane chains to add softness, or other molecules of interest can be attached to the dendrimer so that it becomes a compact carrier.

The payload-containing linear, branched, or lightly crosslinked polymer carriers may be attached to the hair via a mordant or cationic fixing agent. Carboxyl-, phosphate-, phosphonate-, sulfate-, and sulfonate-containing polymers can be complexed with alkaline earth metal that have very low toxicity, such as $Mg^{2+}$, $Ca^{2+}$, and $Sr^{2+}$. Thus, for example, a soluble polymer that contains, for example, carboxyl groups and one or more payloads, such as dye molecules or compounds that add softness, is applied to the hair. In a next step, a soluble calcium or magnesium salt is added to the hair to precipitate the polymer on and in the hair.

In short, the nanoscopic carrier approach provides a flexible, invisible system to color hair. In contrast to traditional chemical assaults, the system is gentle to the hair and the color may be long-lasting or reversed by custom-tailored means.

Nano-Technology Based Softener, Fragrance, and UV Blocking Treatments for Hair

In a manner similar to the dying process described above, the nanoscopic carriers described in this invention may also be used to deposit fragrances, UV absorbers/blockers, and other desirable agents on hair. The carriers may be particulate in shape or simply be a polymer of arbitrary architecture. The use of methods of fixation enabled through the carriers is one part of the innovation.

Silicones and polyolefins impart a soft hand on hair. They may be deposited on hair simply as the carrier itself in the context of this invention. The fixative step is then part of the innovation. For example, in the first rinse a cationic silicone is applied. This coating is then fixed in place in a subsequent rinse containing an anionic silicone, resulting in a complex formation that creates a silicone network on the surface of the hair. Charged polyolefins can be substituted for the silicones in the above example.

In certain instances, such as for example when the payload is a fragrance or a pharmaceutical agent, it is desirable for the payload to be controllably released from the nanostructure on or into the hair. Nanoparticles can be designed so that the payload agent is embedded or entrapped within the polymeric shell or matrix of the nanoparticle but is also able to be released from the nanoparticle in a prolonged or otherwise controllable fashion. The release profile is programmed via the chemistry of the polymer network of the nanoparticle. The nanoparticle can be formulated with an almost infinite degree of designed characteristics via structural features, such as crosslinking density, hydrophilic-hydrophobic balance of the copolymer repeat units, and the stiffness/elasticity of the polymer network (for example, the glass transition temperature). In addition, erodible nanoparticles or other nanostructures can be developed to controllably release the payload.

Furthermore, the polymer matrix may contain components that react or respond to environmental stimuli to cause increased/decreased content release. "Smart polymers" are polymers that can be induced to undergo a distinct thermodynamic transition by the adjustment of any of a number of environmental parameters (e.g., pH, temperature, ionic strength, co-solvent composition, pressure, electric field, etc.). For example, smart polymers based on the lower critical solution temperature (LCST) transition may cut off release when exposed to warm or to hot water during washing. When cooled back to room temperature, sustained release resumes. Smart polymers may be selected from, but are not limited to, N-isopropyl acrylamide and acrylamide; polyethylene glycol, di-acrylate and hydroxyethylmethacrylate; octyl/decyl acrylate; acrylated aromatic and urethane oligomers; vinylsilicones and silicone acrylate; polypropylene glycols, polyvinylmethyl ether; polyvinylethyl ether; polyvinyl alcohol; polyvinyl acetate; polyvinyl pyrrolidone; polyhydroxypropyl acrylate; ethylene, acrylate and methylmethacrylate; nonyl phenol; cellulose; methyl cellulose; hydroxyethyl cellulose; hydroxypropyl methyl cellulose; hydroxypropyl cellulose; ethyl hydroxyethyl cellulose; hydrophobically-modified cellulose; dextran; hydrophobically-modified dextran; agarose; low-gelling-temperature agarose; and copolymers thereof. If crosslinking is desired between the polymers, multifunctional compounds such as bis-acrylamide and ethoxylated trimethylol propane triacrylate and sulfonated styrene may be employed. In presently preferred embodiments, the smart polymers comprise polyacrylamides, substituted polyacrylamides, polyvinylmethyl ethers, and modified celluloses.

Where it is desirable for the payload to be visible (when it is a dye or a UV protector, for example), the nanoparticle will be constructed of optically transparent or translucent material, allowing light to come into contact with the payload and be reflected, refracted or absorbed.

The polymeric set can be chosen to give either hydrophobic or oleophilic nanoparticles, allowing a wider array of bioactive compounds or drugs to be comfortably entrapped within. Where the particles are hydrophilic, they are easily dispersible in a stable aqueous suspension or emulsion by surfactants, which can subsequently be washed away without affecting the performance of the payload agent within. The inherent thermodynamic compatibility of the agents and the polymeric shell or matrix material can increase the loading level per particle.

The following examples are intended to illustrate some, but not all, of the concepts described in this disclosure, and are in no way intended to limit it. One skilled in the art would also see that different ideas from different examples or from the above explanation could be combined to yield other possible ways of treating hair.

EXAMPLES

Example 1

One or more of the same or different dye molecules are covalently bonded, by methods known in the art, to an amine-containing polymer or oligomer such as poly (ethylenimine), poly(allylamine hydrochloride), or poly (lysine). (An oligomer or polymer of arginine would be expected to behave similarly.) Hair is wet with a solution containing this polymer or oligomer with dye molecules pendant on it (a polymeric or oligomeric dye). In some cases it may be necessary to rinse away excess material. To set or cure the amine-containing polymer, the hair is then exposed to a polymer that contains carboxyl, sulfate, sulfonate, phosphate, or phosphonate moieties. Examples of such polymers include DNA, poly(acrylic acid), poly(itaconic acid), poly(maleic anhydride), copolymers containing maleic anhydride units, a polymer with —$C_6H_5COOH$ groups, poly(methacrylic acid), or poly(styrene sulfonate, sodium salt). Excess material is then rinsed away. An electrostatic interaction holds the two polymers together, greatly decreasing the solubility of the complex.

This and all other formulations and solutions mentioned in this document may additionally contain fragrances, wetting agents, oxidizing agents, antioxidants, opacifiers, thickeners, reducing agents, defoamers, surfactants (anionic, cationic, nonionic, amphoteric, zwitterionic, or mixtures thereof), sequestering agents, medicines (drugs), dispersing agents, conditioners, limited quantities of organic solvents, antibacterial agents, preserving agents, and the like, as well as mixtures thereof.

Example 2

One or more dye molecules are covalently bonded to a carboxyl-containing polymer or oligomer such as poly(acrylic acid), poly(itaconic acid), poly(maleic anhydride), a copolymer containing maleic anhydride units, a polymer with —$C_6H_5COOH$ groups, or poly(methacrylic acid). Hair is wet with a solution containing this oligomeric or polymeric dye. Excess material is then rinsed away. To set this polymer, the hair is exposed to a polycation (polymer or oligomer), such as poly(ethylenimine), poly(allylamine hydrochloride), poly(lysine), poly(arginine), or poly(diallyldimethylammonium chloride).

Example 3

Hair is exposed to a solution containing one or more polymeric or oligomeric dyes, as described in Example 1 (polycations). It may be necessary to rinse the hair after this first treatment. The hair is then exposed to a solution that contains one or more polymeric or oligomeric dyes (polyanions), as described in Example 2 and it is rinsed.

Example 4

An alkyl chain, which is defined herein as a linear or branched molecule that contains primarily C, CH, $CH_2$, and $CH_3$ units, is tethered to an amine-containing polymer or oligomer, such as poly(ethylenimine), poly(allylamine hydrochloride), or poly(lysine). Linear or branched siloxane chains may also be added to the amine-containing polymer or oligomer. One or more of the same or different dye molecules may also be added to the polymer, by methods known in the art. Hair is then exposed to this polycation and excess reagent may be rinsed away. The hair is then exposed to a polyanion, which may have alkyl chains, siloxane chains, or dyes tethered to it. One possible polyanion, which may act as a softener, is a copolymer of maleic anhydride and a vinyl ether of the form: $CH_2=CHO(CH_2)_nCH_3$, where n is at least 2, and is preferably greater than 4.

Example 5

An amine-containing dye is reacted with benzoquinone, naphthoquinone, anthraquinone or a derivative thereof to form a polymeric or oligomeric dye. The following are three of the numerous possible adducts.

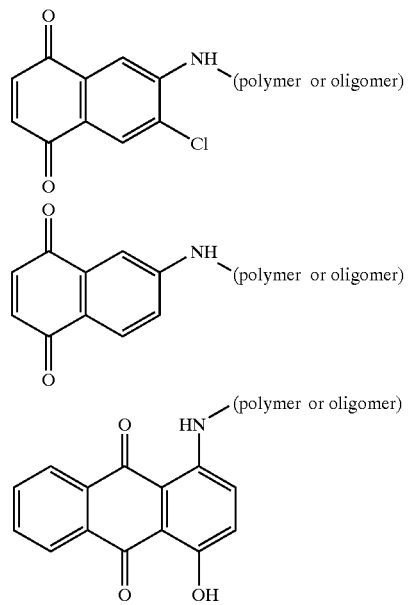

Example 6

An amine-containing dye is reacted with a dye that contains one or more reactive groups such as acid chlorides (—C(O)Cl), sulfonyl chlorides (—$SO_2Cl$), vinyl sulfones (—$SO_2CH=CH_2$), or an active derivative of cyanuric chloride. Examples of each of these four possible linking chemistries for dyes and polymers is shown below. Any other amine-reactive functional groups that may appear on a reactive dye molecule, such as epoxides or acid anhydrides, could be used as well.

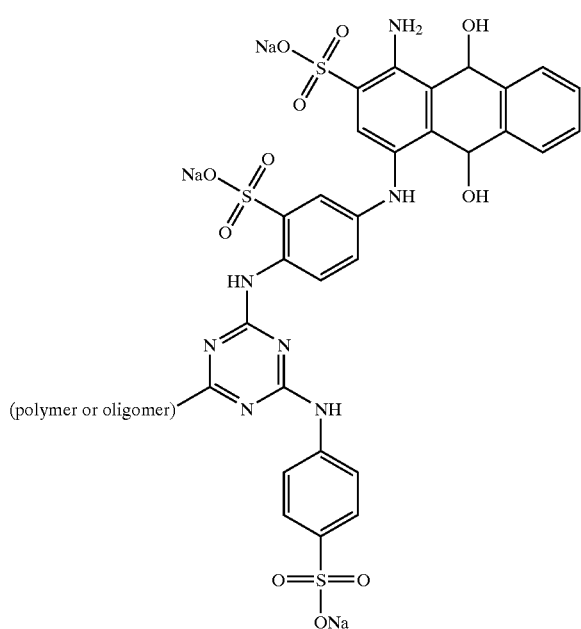

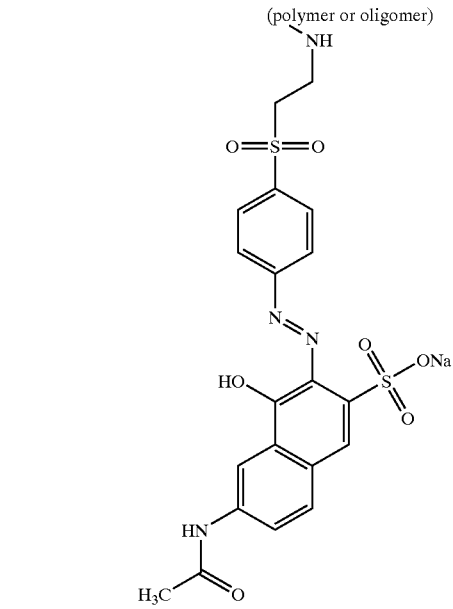

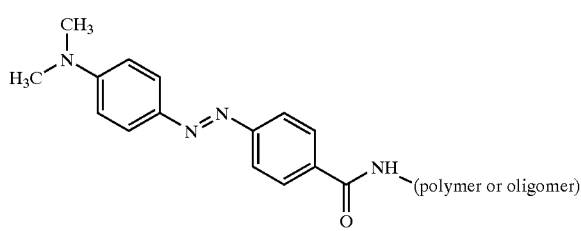

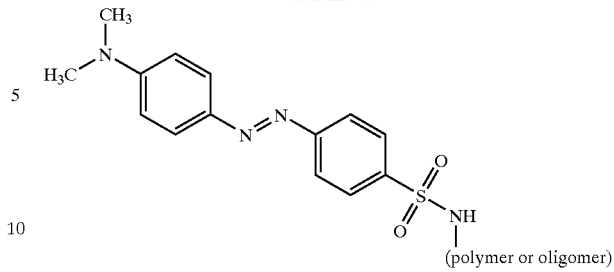

Example 7

A polyelectrolyte containing pendant groups, which modify a property of hair or which add new and desirable properties, is deposited on hair. An oppositely charged polyelectrolyte, which also may contain one or more pendant groups that modify a property of hair or that add a desirable property to hair, is added to the hair, condensing with the first polymer to immobilize it.

Example 8

A polymer or oligomer that contains one or more pendant groups, which modify one or more properties of hair or which add one ore more desirable properties, is deposited on hair. Excess reagent may be washed away from the hair. A mordant, which we define as a species that contains a metal atom with an oxidation number of 2 or higher, is added to the deposited polymer, immobilizing the polymer.

Example 9

A mordant is deposited on hair. Excess reagent may be washed away from the hair. A polymer or oligomer that contains one or more pendant groups which modify one or more properties of hair or which adds one or more desirable properties is deposited on hair. The mordant complexes with the polymer to immobilize the polymer.

Example 10

One or more dye molecules is covalently attached to a polymer or oligomer of ethylenimine, such as triethylenetetraamine (see Reaction Scheme 1). In addition to an ethylenimine, any polymer with free amine groups may be used, including poly(allylamine hydrochloride) and poly(lysine). Additional starting materials include small molecules with multiple amines, such as ethylenediamine, and large polymers of ethylenimine (branched or linear). Amines are well know to react with a variety of dyes. For example, U.S. Pat. No. 6,203,578 shows reactions of amines with benzoquinone, naphthoquinone, and anthraquinone, and some of their derivatives, as well as with dyes that have amine-reactive groups. Other amine-reactive groups that are found on commercially-available reactive dyes include moieties based on vinyl sulfone and cyanuric chloride.

After introduction of the dye to the polymer, a group capable of chelating a metal is introduced. One of the possible ways of doing this is by reaction of the remaining amines on the molecule with an ester of α-chloro, α-bromo, or α-iodoacetic acid. The ester is a protecting group that is removed after addition of the molecule to the polymer. Thus, this triethylenetetraamine-dye adduct is then allowed to react with an ester of α-haloacetic acid (ClCH$_2$C(O)OR, BrCH$_2$C(O)OR, ICH$_2$C(O)OR) (see Reaction Scheme 1). The ester group is then removed by a method known in the art (deprotection), leaving a metal-chelating polymeric dye. Methods for the introduction of the protected metal chelating group and its deprotection are known in the art; see, U.S. Pat. No. 6,080,785. In a preferred embodiment, the ester of the α-haloacetic acid is a methyl ester. For example, ClCH$_2$C(O)OCH$_3$ is an inexpensive chemical that is available in bulk quantities. Note that the carboxymethyl group can be introduced by reaction of formaldehyde and hydrogen cyanide with an amine. The addition of these two reagents to ethylenediamine (the Strecker synthesis) yields ethylenediaminetetraacetic acid (EDTA) (see Beyer and Walter in *Handbook of Organic Chemistry*, Prentice Hall, 1996). Also note that the chelating polymeric dye shown in Reaction Scheme 1 is a close analog of EDTA and nitrilotriacetic acid (N(CH$_2$COOH)$_3$), both of which are effective metal chelators.

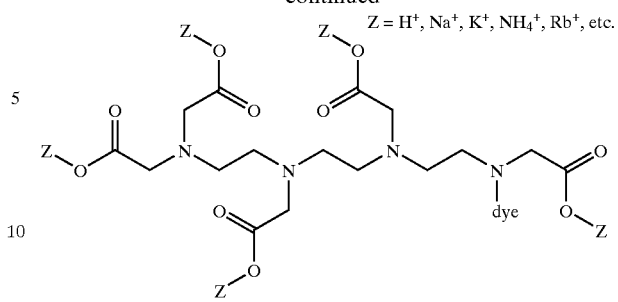

Example 11

This example (see Reaction Scheme 2) demonstrates two important features of the chemistry disclosed herein. First is the ability to immobilize a polymeric dye with a mordant using groups that can chelate a metal. Second is the extraction of the metal atoms from the polymer with EDTA or NTA, which reverses the initial dyeing process. Note that the exact geometry of the metal-polymer complex will vary from metal to metal. Both intramolecular (shown in Reaction Scheme 2) and intermolecular crosslinks between polymeric or oligomeric dye molecules are expected. As is the case for all of the processes shown here, the depth of penetration of the dye into the fiber could be controlled, in part, by the size of the molecule. One or more surfactants or other additives may also be present in this and other formulations (see Example 1).

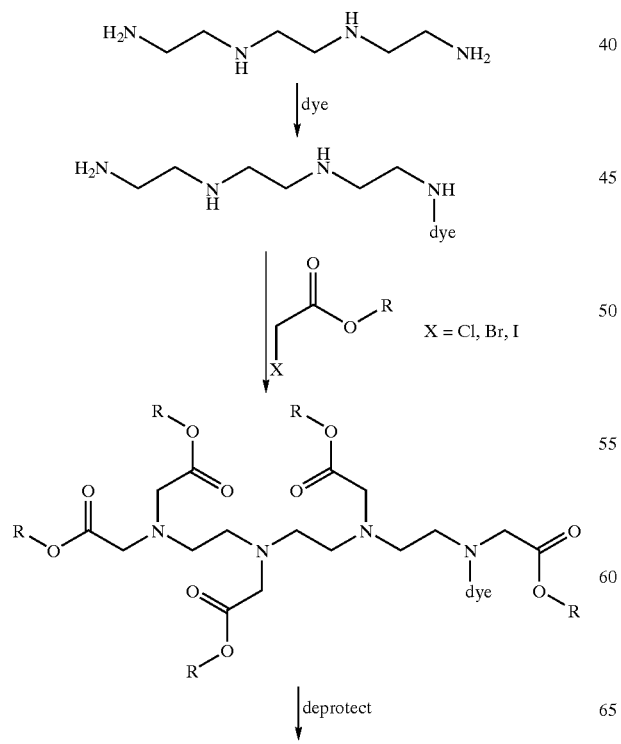

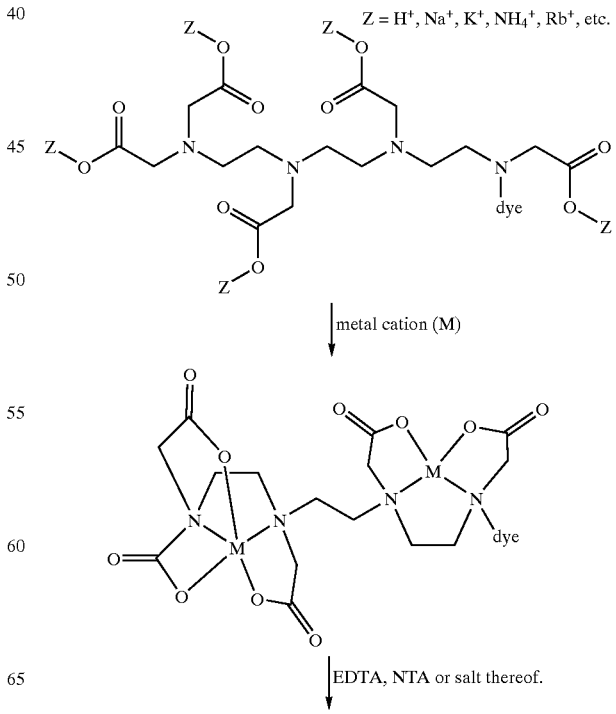

-continued

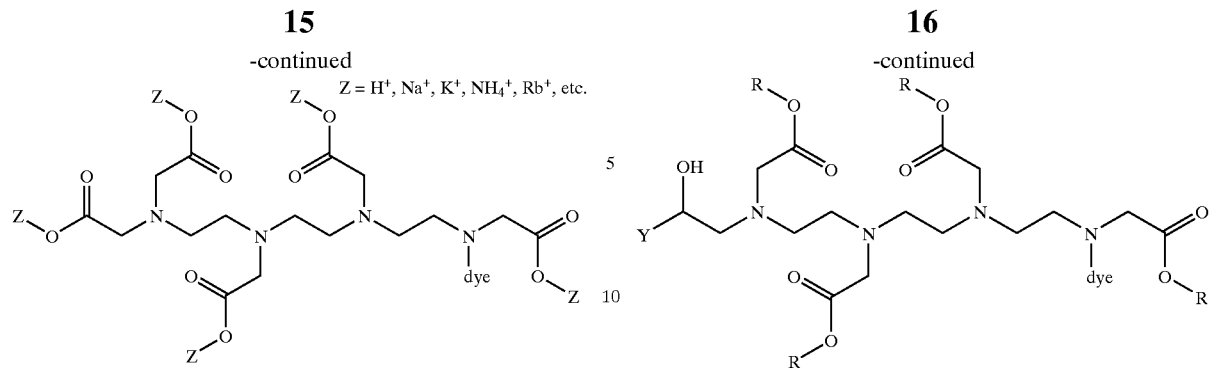

Z = H⁺, Na⁺, K⁺, NH₄⁺, Rb⁺, etc.

Example 12

In this example (see Reaction Scheme 3), a polymeric dye is first created, a softening agent is then added to the oligomeric or polymeric dye, and a chelating group is introduced. Siloxane and alkyl chains are expected to act as softeners, but another important feature of these long chains is to reduce the solubility of the polymeric or oligomeric dye. Thus, when any surfactants in the formulation are removed by rinsing, the polymeric dye may be deposited onto the hair. Addition of metal (shown in Reaction Scheme 4) would act to increase its durability. As was the case in Example 11, the process of adding a metal is reversible using EDTA and NTA (see Reaction Scheme 5). Reaction Scheme 3 shows introduction of an alkyl or siloxane chain with an epoxide group. While epoxide chemistry is a preferred embodiment of the ideas in this example, other possible reactive groups that could be used to introduce long-chain alkyl or siloxane groups by means known in the art include, but are not limited to, anhydrides, acid chlorides, carboxylic acids, sulfonyl chlorides (to make sulfonamides), etc.

Reaction Scheme 3:

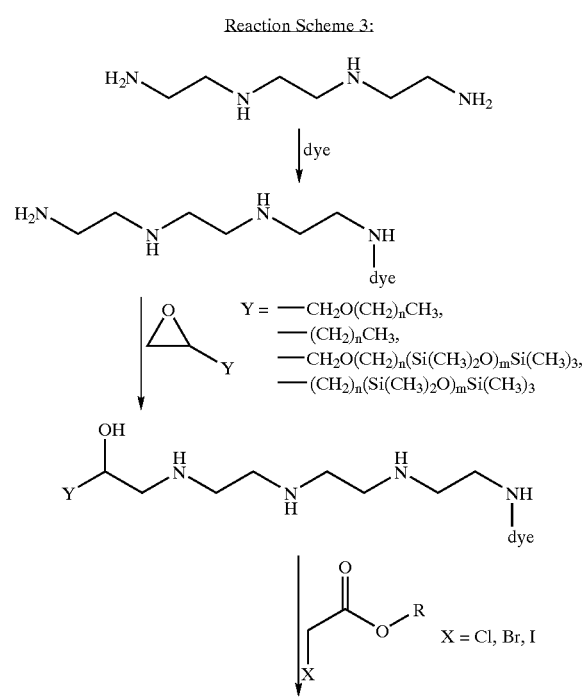

Reaction Scheme 4:

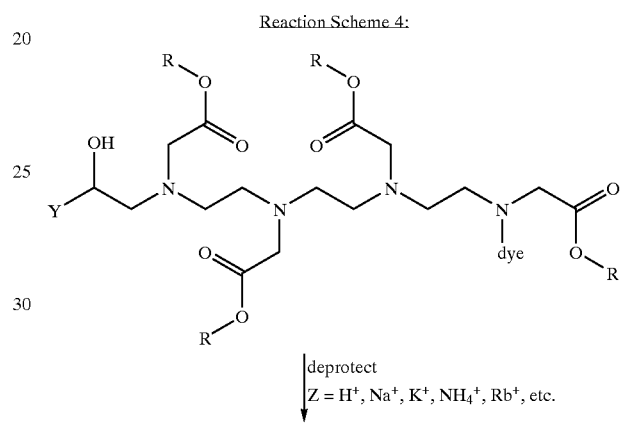

deprotect
Z = H⁺, Na⁺, K⁺, NH₄⁺, Rb⁺, etc.

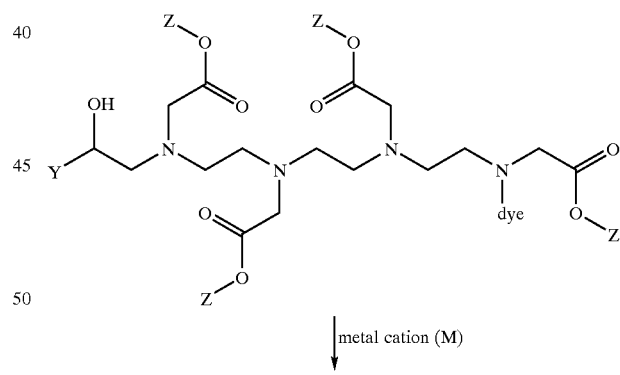

metal cation (M)

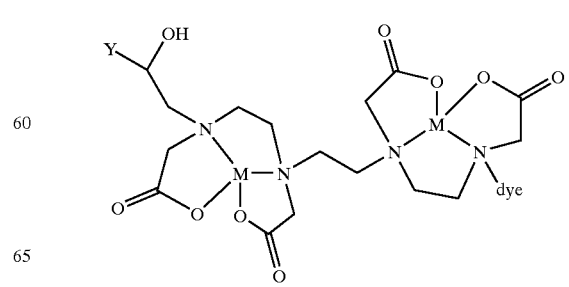

Reaction Scheme 5:

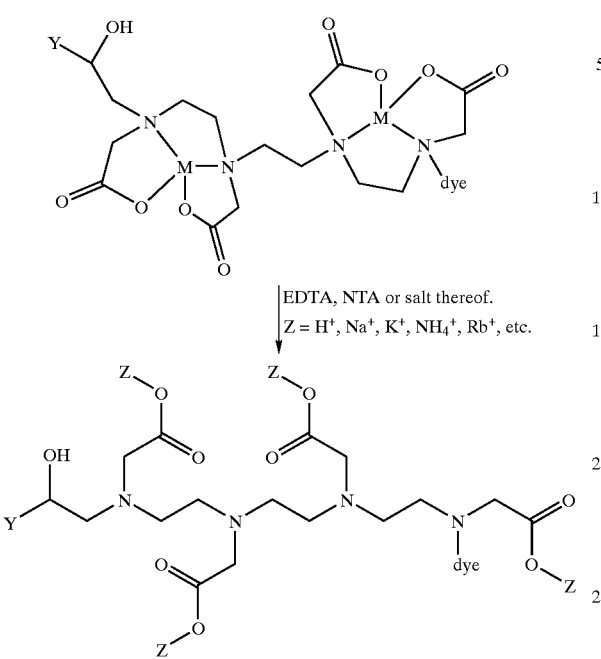

Example 13

A variety of molecules that impart desirable properties to hair or to the formulation can be incorporated into reactive monomers, such as in the reaction between an amine and an acid chloride (see Reaction Schemes 6 and 7). Later it will be possible to polymerize such monomers into polymers that have desirable properties, where the level or concentration of certain groups is carefully controlled.

Reaction Scheme 6:

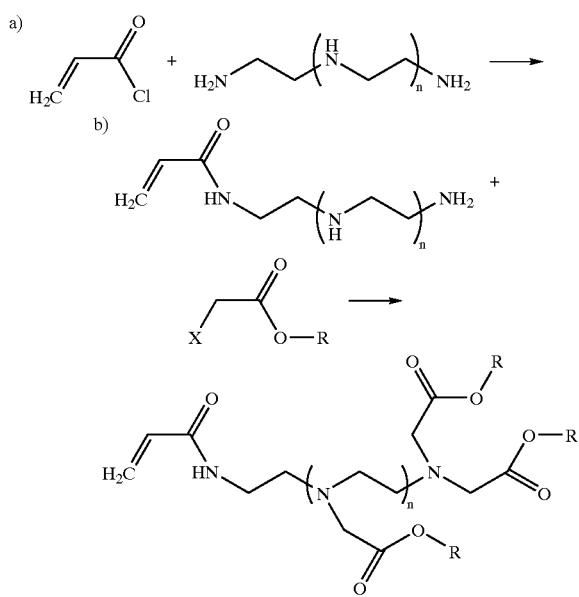

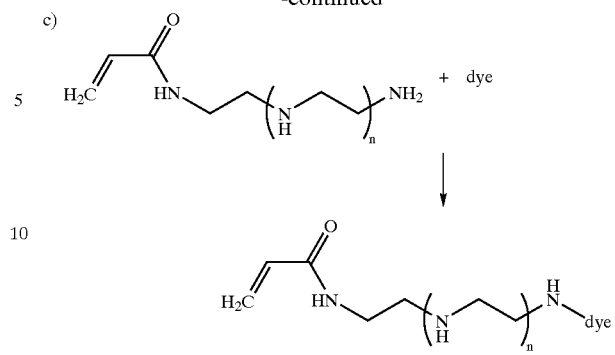

Reaction Scheme 7:

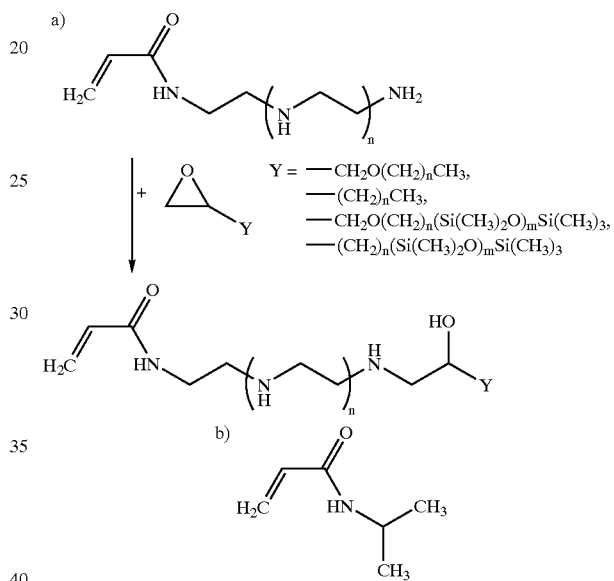

Example 14

N-isopropylacrylamide (NIPA) (see Reaction Scheme 7b) will make a polymer thermally sensitive. In other words, at low temperatures, a polymer that has NIPA (or an analogous monomer) will have a higher water solubility than at higher temperatures. Thus, a polymer can be designed that precipitates when the hair is washed with warm or hot water.

Example 15

In this example (see FIG. 1), a set of molecules, which may be dyes, fragrances, softeners, medicines (drugs), monomers, or other molecules which modify a property of hair or which add new and desirable properties, is emulsified with a polymerizable surfactant. The resulting micelles are then polymerized into a nanoparticle, which can be applied to hair and then, depending on the head group of the surfactant, set with a mordant or a polyelectrolyte with a charge opposite that of the surfactant's head groups. The head groups may be designed to be analogs of EDTA or NTA so that the surfactant will be particularly effective in chelating a metal ion.

Example 16

Derivatives of itaconic anhydride and maleic anhydride can be used as polymerizable surfactants (see Reaction Scheme 8). To produce such surfactants, a fatty alcohol (or amine, which is not shown) can be reacted with the anhydride to produce a surfactant. A carboxyl group is the head group. In its deprotonated form, it will impart a high degree of solubility to the alkyl chain in the surfactant. This head group can be precipitated with an appropriate mordant. In some cases, it may be desirable to create an anionic surfactant by addition of ethylene oxide units to the carboxyl group of the polymerizable surfactant (bottom four structures in Reaction Scheme 8). It is not intended that the present invention be limited to the polymerizable surfactants described in this document. A variety of other polymerizable surfactants have been developed and may be applicable to the situations described herein. A few references showing the syntheses, use, and properties of these materials include: Stähler, et al., Langmuir 1998, 14, 4765–4775; Stähler, et al., Langmuir 1999, 15, 7565–7576; Kline, Langmuir 1999, 15, 2726–2732; Soula and Guyot, Langmuir 1999, 15, 7956–7962; Shen, et al., Langmuir 2000, 16, 9907–9911; Viitala, et al., Langmuir 2000, 16, 4953–4961; Jung, et al., Langmuir 2000, 16, 4185–4195; Gargallo, et al., Langmuir 1998, 14, 5314–5316; Liu, et al., Langmuir 1997, 13, 4988–4994; Xu, et al., Langmuir 1999, 15, 4812–4819.

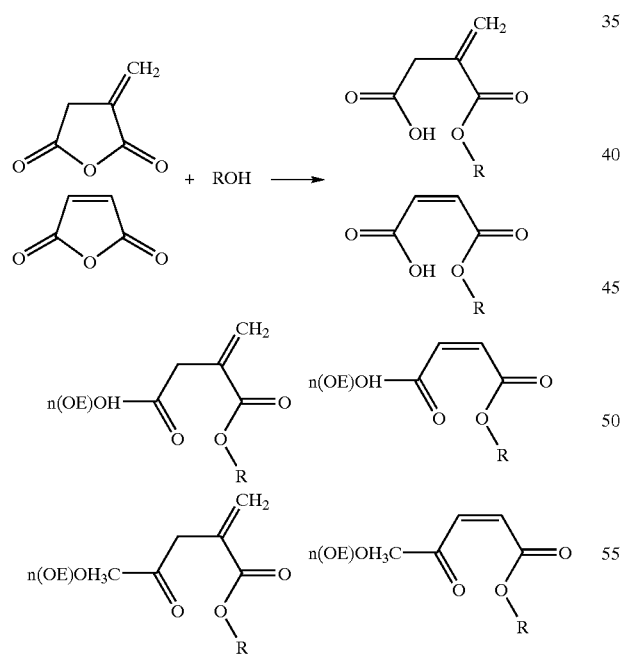

Reaction Scheme 8:

Example 17

A polyamine, which contains two or more amine groups (the amines could be pendant or the spacing between the amines could be three or more carbons, although it is two in the preferred embodiment), is reacted with one or more alkyl or siloxane chains to produce a surfactant (see Reaction Scheme 9). The amines are then derivatized with carboxymethyl groups to form a surfactant that can chelate metals. Thus, a set of dyes, fragrances, softeners, medicines (drugs), or other small molecules or polymers could be brought into solution with this surfactant and the resulting micelles could be precipitated onto hair by using an appropriate mordant. A particularly useful embodiment of this idea is the reaction of ethylenediamine with an oxirane ring (epoxide) on an alkyl or siloxane chain. Carboxymethyl groups are then introduced into the resulting molecule. One or more of the carboxyl groups or the hydroxyl group may be functionalized with ethylene oxide units, as is commonly done with nonionic surfactants.

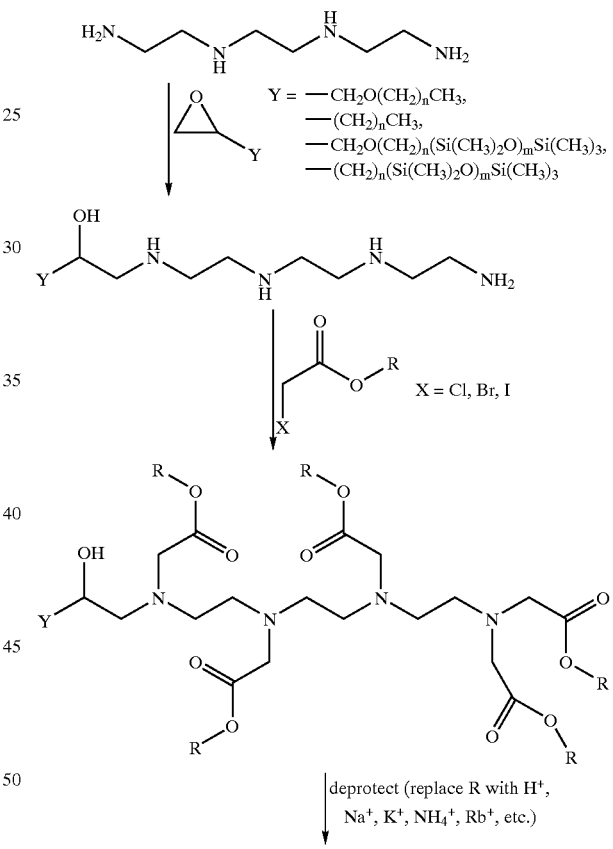

Reaction Scheme 9:

Example 18

A variety of molecules that add desirable properties to a polymer are added to poly(acryloyl chloride), which acts as a scaffold. See Reaction Scheme 10 for examples of a few of the many possible species (amines and alcohols in the preferred embodiment), which could react with poly(acryloyl chloride) to create a functionalized polymer with tailored properties.

Reaction Scheme 10:

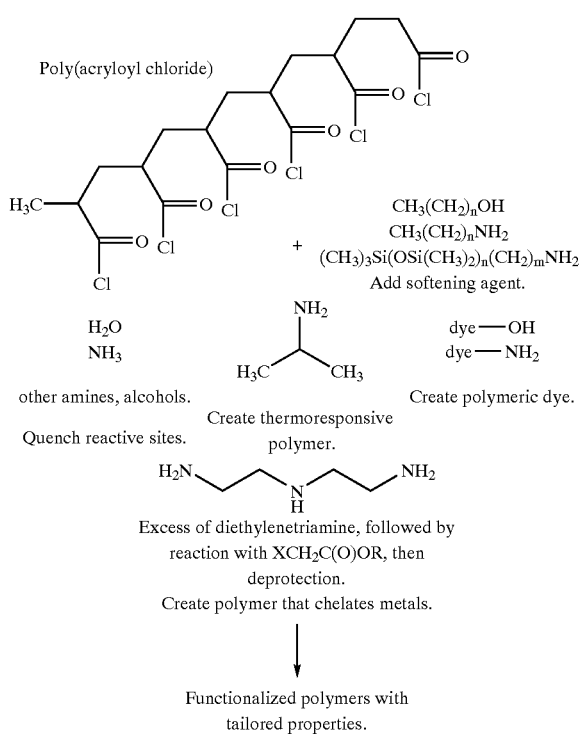

Example 19

A variety of molecules that add desirable properties to a polymer are added to poly(acrylic anhydride), which acts as a scaffold. See Reaction Scheme 11 for examples of a few of the many possible species (amines and alcohols in the preferred embodiment), which could react with poly(acrylic acid) to create a functionalized polymer with tailored properties. Copolymers of maleic anhydride would be expected to react similarly to the polymer shown in Reaction Scheme 11.

Reaction Scheme 11:

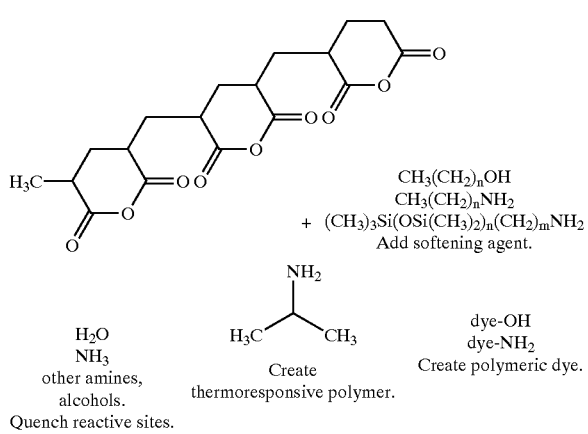

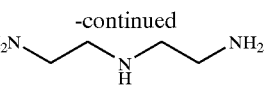

Excess of diethylenetriamine, followed by reaction with XCH$_2$C(O)OR, then deprotection.

Create polymer that chelates metals.

Functionalized polymers with tailored properties.

Example 20

A fatty amine with the general formula $CH_3(CH_2)_nNH_2$, although branched alkyl chains are also possible, is derivatized with carboxymethyl groups according to the methods described in this document to yield a surfactant with the formula: $CH_3(CH_2)_nN(CH_2COOH)_2$. One or both of the carboxyl groups in this surfactant can be deprotonated. A set of small molecules, which may include dyes, fragrances, softeners, medicines (drugs), monomers, etc., is made soluble with this surfactant. The resulting micelles are then precipitated onto hair with a mordant. Because this surfactant can be rendered insoluble by chelating it with an appropriate metal, this surfactant could be generally useful in any situation where it is desirable to remove a surfactant from a formulation. As is the case for nonionic surfactants, some ethylene oxide units may be added to this surfactant. It is expected that mordant crosslinking with chelating surfactants will be of intermediate effect in limiting the release of small molecules captured in micelles by these surfactants. Thus, capture and immobilization of small molecules by this method may provide an effective means of allowing time release of certain small molecules such as fragrances and medicines (drugs). Surfactants with different chelating powers (note those in Example 17 and Reaction Scheme 9) could be combined to fine tune properties of time-release formulations.

Example 21

A set of one or more surfactants is used to bring one or more insoluble or quite insoluble species, including polymers and oligomers, into aqueous solution. Upon rinsing away the material, the insoluble or nearly insoluble species are deposited onto hair.

Example 22

A known dye molecule, including, but not limited to acid dyes, direct dyes, reactive dyes, mordant dyes, sulfur dyes, and vat dyes, is reacted with a polymer and the polymer is deposited on hair by one of the methods described in this document.

Example 23

A mordant dye is coupled to a polymer or oligomer and this material is deposited on hair. Addition of a mordant causes crosslinking of the polymer molecules through the mordant dye pendant groups.

Example 24

A protein, which acts as a scaffold, is derivatized with dye molecules, softeners, a polyelectrolyte oligomer chain, carboxymethyl groups or other species that may impart a desirable property to hair. The resulting protein complex is then precipitated onto hair and immobilized to one degree or another with the methods described herein, e.g., a polyelectrolyte or a mordant.

What is claimed is:

1. A method of treating hair which comprises, applying a hair treatment preparation to the hair, the hair treatment preparation comprising a payload covalently attached to a polymeric nanostructure, the polymeric nanostructure being reactive to hair or capable of being immobilized onto or in the hair; and changing the conditions such that the payload and nanostructure are attached to the hair.

2. A method according to claim 1 wherein the nanostructure comprises hair-reactive functional groups that, under the change in conditions, will covalently bond to the hair.

3. A method according to claim 1 wherein the nanostructure comprises functional groups that are electrostatically interactive with complementary groups on the surface of the hair when, under the change of conditions, the ionic strength or suafactant content is shifted by rinsing, and the change in conditions is rinsing the hair.

4. A method according to claim 3 wherein the electrostatic interaction is selected from the group consisting of charge-charge, dipolar, hydrogen-bonding, hydrophobic, and dehydration interactions.

5. A method according to claim 1 wherein the nanostructure is a polyelectrolyte and the change in conditions is exposure of the nanostructure to a polyelectrolyte of opposite isoelectric point to form a complex coating the treated hair.

6. A method according to claim 1 wherein the hair treatment preparation further comprises a surfactant, and the nanostructure is in a finely divided dispersion; and the change of conditions is rinsing away the surfactant, leaving the nanostructure adhering to the treated hair.

7. A method according to claim 1 wherein the nanostructure is dispersed in a medium, and the change of conditions is a change in the thermodynamic balance of the medium, causing the nanostructure to be deposited on the surface of the treated hair.

8. A method according to claim 1 wherein the nanostructure comprises functional groups that are reactive with a species that contains a metal atom with an oxidation number of 2 or higher, and the change of conditions is the application of said species to the hair to form a complex with the nanostructure to coat the treated hair.

9. A method according to claim 8 wherein the nanostructure is a crosslinkable surfactant comprising functional groups that are reactive with a species that contains a metal atom with an oxidation number of 2 or higher.

10. A method according to claim 1 which comprises the further step of reversing the change of conditions, such that the payload and nanostructure are detached from the hair.

11. A method according to claim 1 wherein the nanostructure is a nanoparticle.

12. A method according to claim 11 wherein the nanoparticle is optically transparent or translucent.

13. A method according to claim 1 wherein the nanostructure is a nanoscopic network.

14. A method according to claim 13 wherein the nanoscopic network is selected from the group consisting of a linear polymer, a branched polymer, and a highly branched polymer.

15. A method according to claim 1 wherein the nanostructure comprises a smart polymer.

16. A method according to claim 1 wherein the payload is selected from the group consisting of dyes, coloring agents, pigments, opacifying agents, blocking agents, UV absorbers/blockers, scents, fragrances, drugs, pharmaceuticals, softener, insect repellents, antibacterials and antimicrobials.

17. A method according to claim 1 wherein the payload is a dyestuff.

18. A method according to claim 17 wherein the nanostructure is a nanoparticle.

19. A method according to claim 17 wherein the nanostructure is a nanoscopic network.

* * * * *